United States Patent [19]

MacKay et al.

[11] Patent Number: 5,261,406
[45] Date of Patent: Nov. 16, 1993

[54] WHOLE BODY IMAGING SYSTEM

[75] Inventors: Scott MacKay, Ann Arbor, Mich.; Michael K. O'Connor, Rochester, Minn.

[73] Assignee: Medasys Inc., Ann Arbor, Mich.

[21] Appl. No.: 641,263

[22] Filed: Jan. 15, 1991

[51] Int. Cl.$^5$ .............................. A61B 6/00
[52] U.S. Cl. ................ 128/654; 128/653.1; 128/659; 250/363.02
[58] Field of Search ............. 128/653.1, 654, 659; 424/1.1, 4, 9; 250/363.01, 363.02

[56] References Cited

U.S. PATENT DOCUMENTS

| 4,048,296 | 9/1977 | Wolfangel | 424/1.1 |
| 4,500,507 | 2/1985 | Wong | 424/1.1 |
| 4,657,755 | 4/1987 | Christensen et al. | 424/1.1 |
| 4,682,604 | 7/1987 | Fymat et al. | 128/659 |
| 4,709,703 | 12/1987 | Lazarow et al. | 128/654 |
| 4,755,679 | 7/1988 | Wong | 128/654 |
| 5,024,230 | 6/1991 | Lindstrom et al. | 128/659 |
| 5,024,233 | 6/1991 | Simecek et al. | 128/659 |
| 5,027,817 | 7/1991 | John | 128/654 |

Primary Examiner—Lee S. Cohen
Assistant Examiner—Krista M. Pfaffle
Attorney, Agent, or Firm—Harness, Dickey & Pierce

[57] ABSTRACT

A system and method for the quantitation of whole body distribution of radiopharmaceuticals which can determine the percentage uptake of the radiopharmaceutical in a selected region of the body. The system obtains anterior and posterior views of the body using a scintillation camera. These views are then lined up and the geometric mean of the activity at each pixel location is determined. This normalizes the data to produce an activity level which would result if the organ studied were at midpoint of the body. As a result, fast and accurate results are obtained even for organs that are well visualized in only one of the anterior or posterior views.

11 Claims, 9 Drawing Sheets

```
Name:    None                        52
Number:  None
Visit:   None
Study:   None Ant.    Post.   Mean
Body Counts   -----   -----   -----
Bkg. Corr.    -----   -----   -----

Raw Organ     -----   -----   -----
Bkg. Corr.    -----   -----   -----
% Whole Body  -----   -----   -----
```

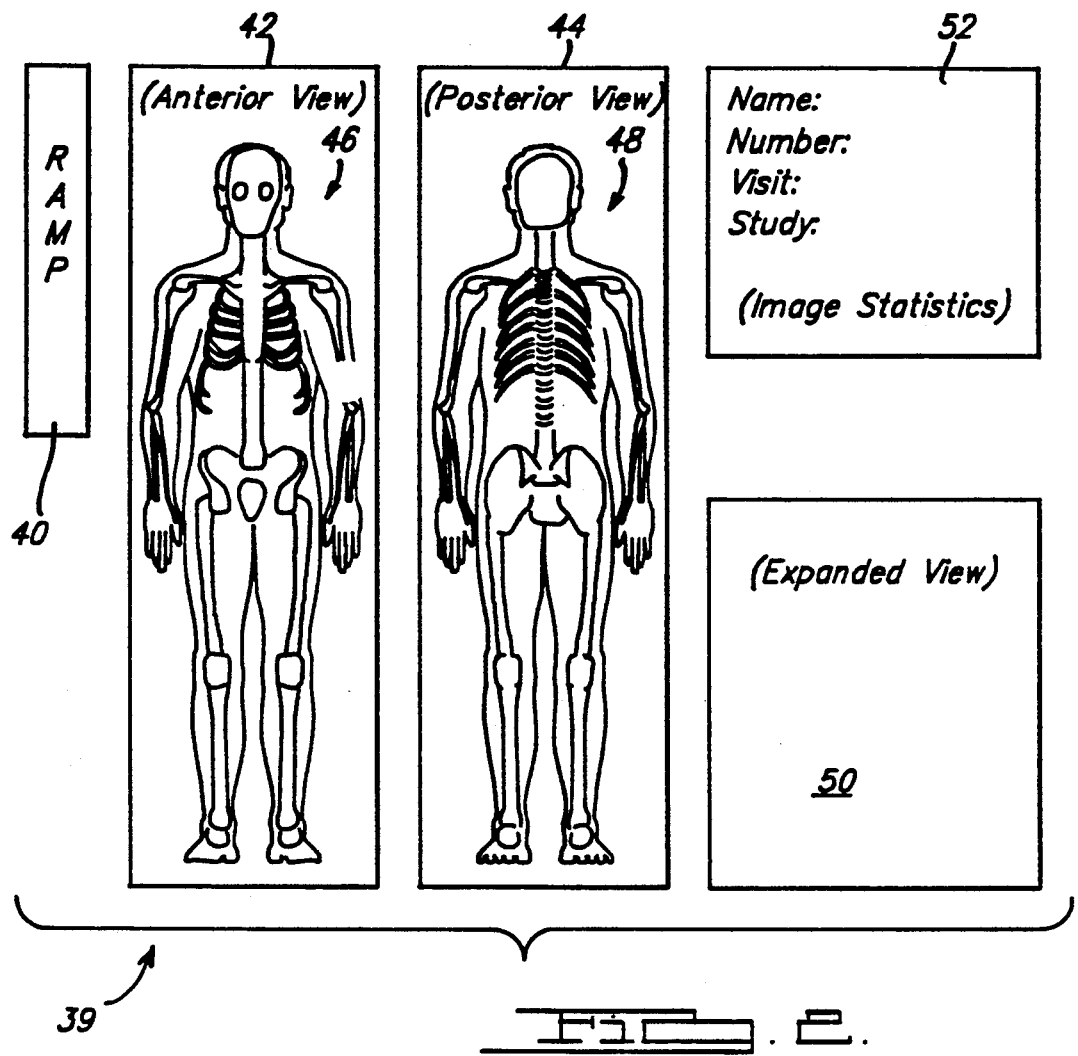

Whole Body Processing

Whole Body Processing

A — Anterior View
Image:
Background:
Organ:                         66

P — Posterior View
Image:
Background:
Organ:                         68

G — Geometric Mean
Image:
Background:
Organ:                         70

N — New Patient
Name:
Number:
Visit:
Study:                         62

63
65
| D — Define Active Area |
| R — Region Statistics |
| E — Expand View    67 |
| S — Save Expanded View |

Create Image
Type the process and image names where the image will be saved.

Process Name:   Whole Body Processing
Image Name:     Geometric Mean Body

Create New Image

FIG. 6.

Select Patient                                    Tue. 09/11/1990 18:05:54

| Sel | | Level | Name | Number Type | Date – Time |
|---|---|---|---|---|---|
| 1 | QC:ORB1/MOFS/A/C057/12 | | | | 01/19/90 21:24:00 |
| 2 | WHOLE BODY ACQUSITIONS | | | 999-99-9999 | 01/01/90 01:01:00 |
| 3 | WORKSTATION | | | WORK FILES | 01/01/90 01:01:01 |

Patient Utility Actions

| | Default/Input/Form | Memory/Output/To |
|---|---|---|
| | Node: N/A | Node: N/A |
| Init | Supervisor | Supervisor |
| Select | Data Directory | Data Directory |
| Path | Workstation Default | Workstation Default |
| Xchange | | |

Manual Positioning

Expanded Region Selection

Position box so that it encloses the part of the body which is to be displayed as the expanded region.

Expanded region pixels:     1 to 128

MOUSE HELP

| Action | Button | Direction |
|---|---|---|
| Move Box | Button 1 | Up/Down |
| Done | Tap 1 (or "End" Key) | N/A |
| Abort | Tap 2 (or "Esc" Key) | N/A |

Rectangle Position

Rectangle Position

Position rectangle so that it just touches the edges of the feature of interest.

MOUSE HELP

| Action | Button/Key | Direction |
|---|---|---|
| Position Rectangle | None | All Directions |
| Size Rectangle | Button 1 | All Directions |
| Done | Tap 1 (or "End" Key) | N/A |
| Abort | Tap 2 (or "Esc" Key) | N/A |

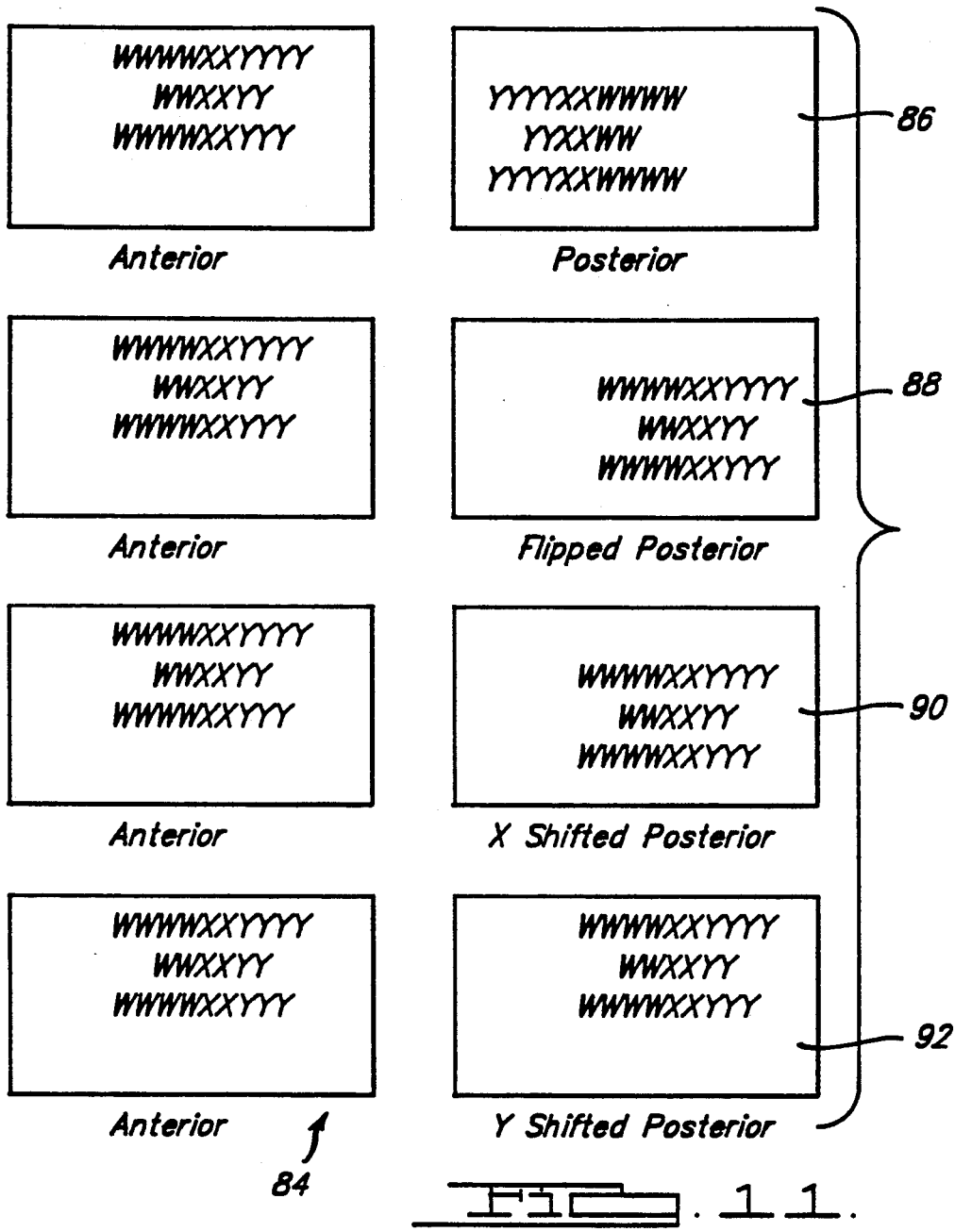

Rectangle Position

Rectangle Position

Position rectangle so that it just touches the edges of the active area.

MOUSE HELP

| Action | Button/Key | Direction |
|---|---|---|
| Position Rectangle | None | All Directions |
| Size Rectangle | Button 1 | All Directions |
| Done | Tap 1 (or "End" Key) | N/A |
| Abort | Tap 2 (or "Esc" Key) | N/A |

Old Or New

Selecting a region study

Do you want to create a new region, or load a previously created ROI?

| Create New ROI | Load "Old" ROI |
|---|---|

Load Regions

Loading a region of interest

Type of ROI:    Background         Organ

Active View:    Anterior    Posterior    Geo. Mean

Load Region

```
┌─ Create ROI ─────────────────────────────────────────┐
│ │      Creating a region of interest              │ │
│ ├──────────────────────────────────────────────────┤ │
│ │                                                  │ │
│ │ Process Name:   Whole Body Processing            │ │
│ │ Region Name:    Anterior Background              │ │
│ │                                                  │ │
│ │ Type of ROI:    Background            Organ      │ │
│ │ Active View:    Anterior    Posterior Geo. Mean  │ │
│ │ Method:         Outline     Irregular Box        │ │
│ ├──────────────────────────────────────────────────┤ │
│ │              Create New Region                   │ │
└──────────────────────────────────────────────────────┘
 112

FIG. 16.

┌─ Save Regions ──────────────────────┐
│  Do you also want to save the ROIs? │   114
├─────────────────┬───────────────────┤
│      Yes        │        No         │
└─────────────────┴───────────────────┘

FIG. 17.

┌─ Create Image ROI ──────────────────────────┐
│  Type the image name for the expanded       │
│  region.                                    │   116
├─────────────────────────────────────────────┤
│                                             │
│  Process Name:   Whole Body Processing      │
│  Image Name:     Anterior Lines 1-128       │
│  Region Name:    Anterior Lines 1-128       │
│                                             │
│             Create New Image                │
└─────────────────────────────────────────────┘

FIG. 18.
```

WHOLE BODY IMAGING SYSTEM

BACKGROUND OF THE INVENTION

1. Technical Field

This invention relates to systems and methods for the quantitation of whole body distribution of radiopharmaceuticals in nuclear medicine, and in particular to a system for determining the percentage uptake of a radiopharmaceutical in a selected region of the body.

2. Discussion

The field of nuclear medicine has developed imaging techniques which make it possible to examine functions of the human body non-invasively. This has resulted in great advances in medical diagnosis, treatment, and research. In nuclear medicine, the body is viewed as a complex array of coordinated and physical motions, making possible a new approach to disease and providing the ability to recognize disease at a much earlier functional stage, even before detectable structural changes have occurred. One example is bone imaging, which can detect some focal diseases even before microscopic changes can be detected.

In a typical nuclear imaging examination, a tracer comprised of a radioactive isotope is given, usually by injection into an arm vein, and the distribution of the radioactive substance within the body or a part of the body is portrayed in a series of nuclear images. These images, which result from the emission of gamma rays by the tracer substance passing out of the body, are recorded by a scintillation camera. A scintillation camera is a radiation detection device, typically consisting of a large sodium iodide crystal which detects the gamma rays that interact with the crystal by detecting the photons produced in this interaction. In this way, the scintillation camera locates where on the detector face the interaction occurred. These interactions are used to produce a picture, or image, of where the gamma rays originated within the body. These images are similar to those in routine x-ray examinations, except that gamma rays are emitted from the body to provide the diagnostic information, rather than being transmitted through the body. Nuclear images depend on specific radioactive elements or compounds labeled with radioactive elements being selectively concentrated in an organ, making it possible to obtain pictures that provide information about regional function within the organ.

In many nuclear imaging techniques, besides the information gained from viewing the resulting image, it is frequently desirable to quantify the amount of the radiopharmaceutical which has been absorbed in a particular region of the body. For example, by knowing the total amount of gamma rays emitted from the body (as measured by the number of counts detected by the scintillation camera over the whole body) and by knowing the total number of counts emitted by one portion of the body such as the kidney, the percentage uptake of the radio-pharmaceutical by the kidney can be determined. This percentage can then be used in diagnosis, or in therapy. In diagnosis, the percentage uptake by the kidney may be compared with the percentage expected from a normal kidney. In therapy, the percentage uptake by the kidney can be used to determine how much of a total isotope will be taken up by a cancerous kidney, for example, in the treatment of this cancer. Prior techniques for quantitation of organ activity as a percentage of whole body activity generally use techniques which analyze individual anterior and posterior images of the body using conventional region of interest (ROI) techniques. Unfortunately, these techniques are time consuming and potentially inaccurate, particularly for organs that are well visualized in only one view. This is because the lack of visual information hampers the ability to accurately place the ROI. Accordingly, it would be desirable to provide a technique for quantitation of organ activity as a percentage of whole body activity of a radiopharmaceutical that is relatively fast and which produces accurate results. Further, it would be desirable to provide such a system which produces accurate results even for organs that are well visualized in only one view.

SUMMARY OF THE INVENTION

Pursuant to one embodiment of the present invention, a method is disclosed for determining the percentage uptake of a radio pharmaceutical in a selected region of a body. The method includes the steps of administering the radiopharmaceutical to a person, and measuring the number of counts on a scintillation detector emitted by the person's body at individual coordinate, or pixel, locations from both anterior and posterior views. In this way, anterior and posterior images of the body are created. Next, for each anterior coordinate location the corresponding posterior coordinate location is determined. Then, the geometric mean of the anterior and posterior counts for each coordinate location is calculated. Finally, the total number of geometric mean counts in a selected region is divided by the total number of geometric mean counts in the whole body to determine the percentage uptake of the radiopharmaceutical in the selected region.

In accordance with another embodiment of the present invention, a system is provided for determining the percentage uptake of a radiopharmaceutical in a selected region of a person's body. The system includes a scintillation detector means to measure the number of counts emitted by the body at individual coordinate locations from anterior and posterior views to create anterior and posterior images of the body. Also, the system includes a means for determining the posterior coordinate location for each corresponding anterior location. In addition, the system includes a means for calculating the geometric mean of the anterior and posterior counts for each coordinate location. In addition, the system includes a means for dividing the total number of geometric mean counts in the selected region by the total number of geometric mean counts in the whole body to determine the percentage uptake of the radiopharmaceutical in the selection region.

As a result, the method and system of the present invention enables the determination of the percentage uptake of a radiopharmaceutical in a selected region of the body in a manner which is relatively quick and accurate. In addition, the present invention works well for organs that are well visualized only in one view.

BRIEF DESCRIPTION OF THE DRAWINGS

The various advantages of the present invention will become apparent to one skilled in the art by reading the following specification and by reference to the following drawings in which:

FIG. 1 is a diagram of the main components of the whole body imaging system in accordance with the present invention;

FIG. 2 is an example of a graphics screen layout of the whole body imaging system in accordance with the present invention

FIG. 5 is a diagram of the whole body processing main panel in accordance with the present invention;

FIG. 6 is an example of a patient utilities menu in accordance with the present invention;

FIG. 7 is an example of a screen used for creating or loading a geometric mean image;

FIG. 8 is an example of a screen used for selecting a whole body image name;

FIG. 9 is an example of a screen for selecting an expanded region;

FIG. 10 is an example of a screen for boxing a common feature;

FIG. 11 is a n example of the process of aligning a boxed feature;

FIG. 12 is an example of a screen for selecting an image to view;

FIG. 13 is an example of a screen for defining an area of interest;

FIG. 14 is an example of a screen for creating or selecting a region of interest;

FIG. 15 is a example of a screen for loading a region of interest;

FIG. 16 is an example of a screen for creating a region of interest;

FIG. 17 is an example of a screen for saving regions; and

FIG. 18 is an example of a screen for naming a saved expanded view.

DESCRIPTION OF THE PREFERRED EMBODIMENT

Figure 3:
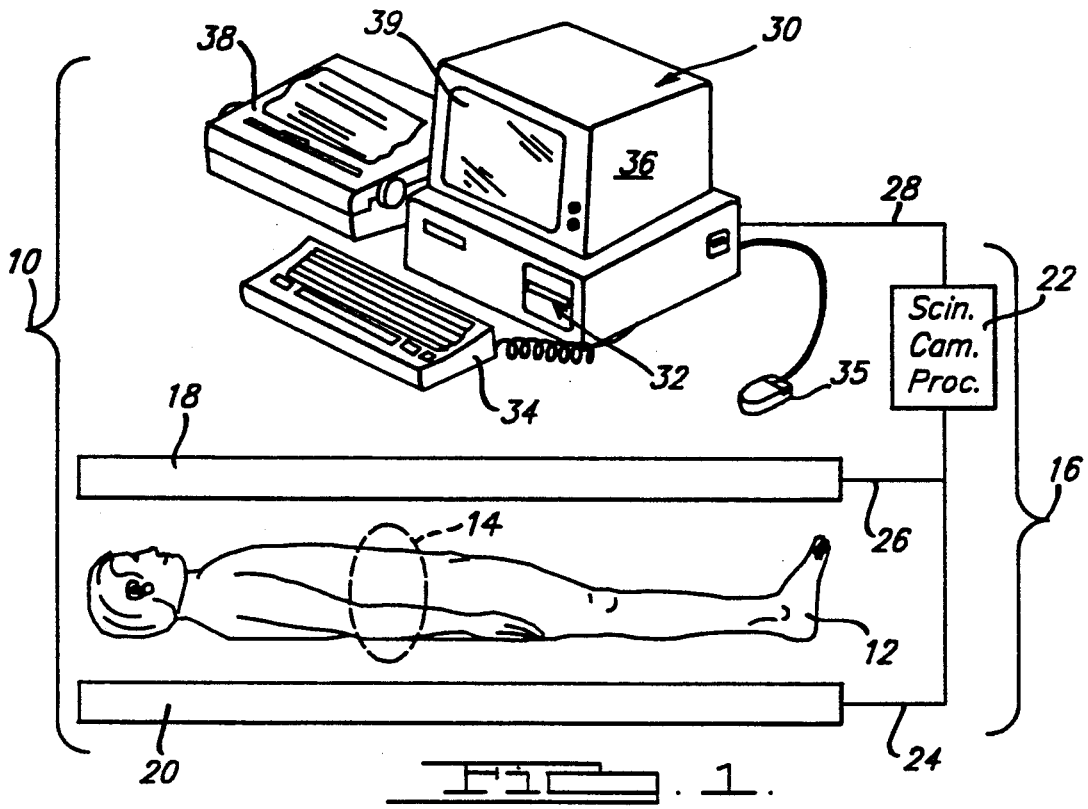
FIG. 3 is a display of the statistics area of the screen layout shown in FIG. 2.

Referring to FIG. 1 a whole body imaging system 10 in accordance with the present invention is shown. This system 10 may be used to obtain quantitative statistics on the relative uptake of a radiopharmaceutical. The system 10 is used by administering a radiopharmaceutical to a person 12 when it is desired to obtain information about radiopharmaceutical uptake in a particular region of interest 14 for the purpose of diagnosis or treatment.

The radiopharmaceutical (not shown) is administered to the person 12 orally or by means of injection, and sufficient time is allowed to permit the radiopharmaceutical to reach a study state distribution within the body. It will be appreciated that radiopharmaceuticals have affinities to particular parts of the body, and as a result, the radiopharmaceutical will be concentrated in different parts of the body differently. The radiopharmaceutical typically emits gamma rays which pass out of the person's body 12 where they are detected by a scintillation camera 16.

The scintillation camera 16 may comprise, for example, a model 55 50 439 manufactured by Siemens of Hoffman Estates, Ill. The scintillation camera 16 uses two heads 18 and 20 which may comprise, for example, large sodium iodide crystals. The detection heads 18 and 20 detect the gamma rays emitted from the body 12 and converts the gamma rays into a stream of photons which are detected and transmitted to the scintillation camera processor 22 along signal lines 24 and 26. It will be appreciated that the scintillation camera 16 is able to detect and process photon counts for a large number of pixels at individual coordinate locations in a region covering the entire body of the person 12.

The scintillation camera 16 is connected by information bus 28 to a central processor 30 which contains the whole body imaging system software 32 in accordance with the present invention. The user of the whole body imaging system 10 interfaces with the system by means of a keyboard 34, a mouse 35, a CRT 36 and a printer 38. For example, CRT 36 may display both anterior and posterior images of the person 12 as processed by the scintillation camera 16. These images may have a resolution of 128 by 512 pixels in an area covering the entire body of the person 12.

Further details of examples of these images and a preferred embodiment of the screen 39 layout on the CRT 36 created by the whole body imaging system software 32 is shown in FIG. 2. This graphics screen is split up into five areas. The ramp or color bar 40 is used to indicate the relationship between the color of a point in an image and the relative level of activity at that point. Two whole body image areas 42 and 44 are used to display one of the three possible views, anterior, posterior, or geometric mean. Examples of whole body images 46 and 48 are shown in FIG. 2. These views 46, 48 may be either displayed as they were acquired, for example as 128×512 acquisitions, or may be compressed before being displayed for 256×1,024 acquisitions. Compression is accomplished by adding adjacent pixels on each line and then adding adjacent lines. Compression is only performed for display and all calculations are performed on the original data.

Images are displayed as required using a first in, first out method. That is, if a position is free (nothing displayed), then the view is displayed in the free position. If neither position is free, the view replaces the view which has been displayed for the longest period of time. An expanded view portion 50 of screen layout 39 is used to display greater detail, to box the feature used when creating the geometric mean, and when creating regions of interest (ROIs) which may comprise, for example, the circled area of the person 12. If a 256×1,024 acquisition is displayed, the expanded region can be used to display a quarter of the view at its full resolution. When creating ROIs or boxing features, the expanded view 50 allows greater accuracy in region placement.

A statistics area 52 displays relevant statistics on the displayed views. Further details of an example of a statistics display 52 is shown in FIG. 3. It is assumed that the anterior and posterior images were acquired at the same time and under the same study. If they were not, the visit and study of the most recently selected view is displayed. The user is not permitted to select views from different patients. The body counts (photon counts from the scintillation camera 16) for a view are calculated each time the view is selected. These body counts include only those counts which are within the "active area". (See discussion of active area below). If an organ region of interest is displayed, its counts are also displayed on area 52. A background region of interest is a representative portion of the area within the image which only contains activity due to scatter within the patient's flesh (i.e. background activity). If a background region of interest is displayed, the background corrected counts for both the whole body and the organ are displayed. The background corrected counts consist of the counts within a region after correcting for background activity. If the background corrected counts are less than or equal to zero or an ROI is not displayed, the appropriate field is filled with "----". The percentage of background corrected counts within the area that is within the organ region of interest is also displayed. If a background region of interest is not displayed, then the percentage within the uncorrected region is displayed.

Figure 4:
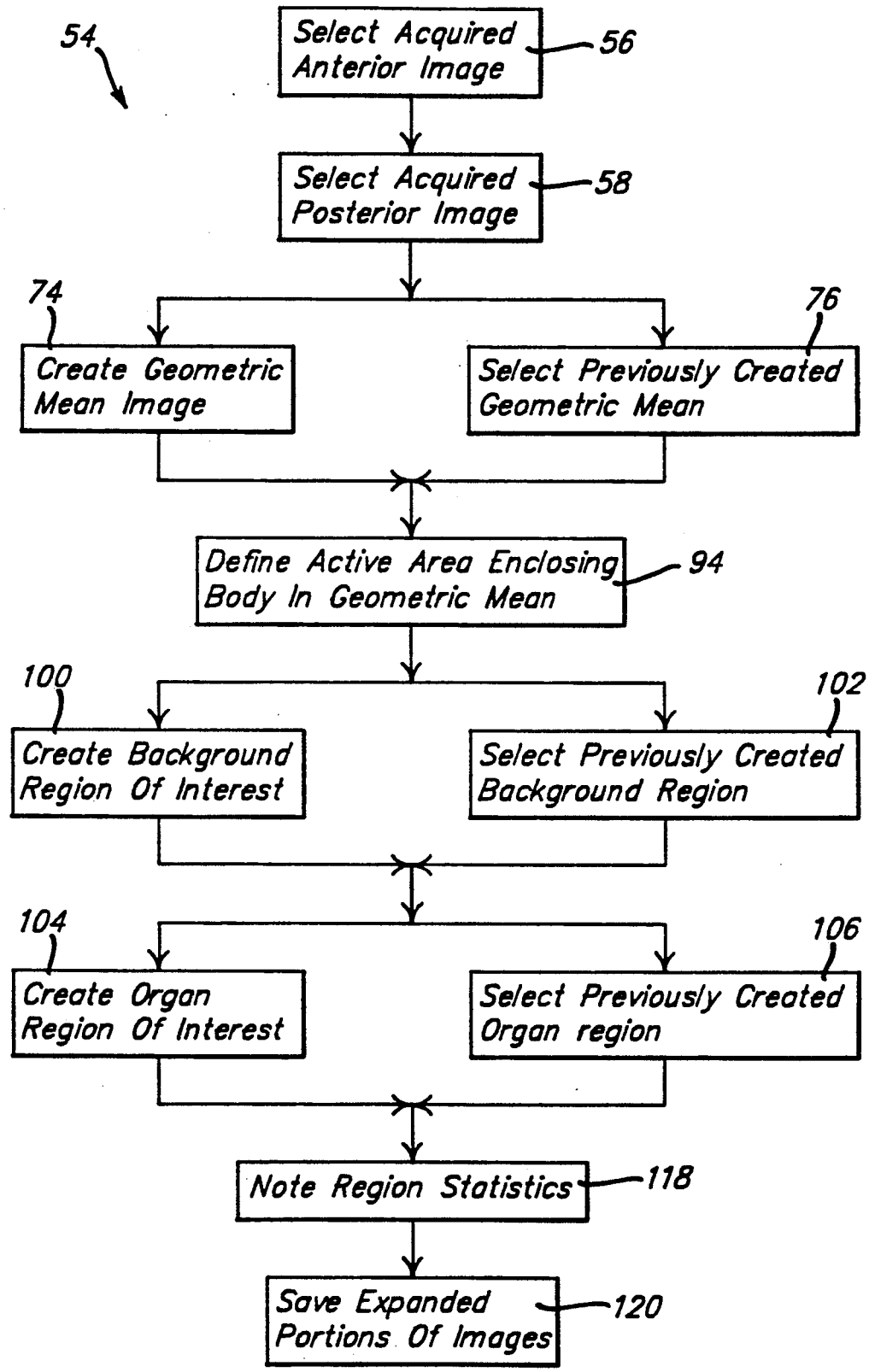
FIG. 4 is a generalized flow diagram of the main steps performed in accordance with the method for whole body imaging of the present invention.

Referring now to FIG. 4, the generalized program flow 54 of the method in accordance with the present invention is shown. Once the scintillation camera 16 has acquired posterior and anterior images, and made them available to the central computer 30, the user first selects an acquired anterior image in block 56, and then selects an acquired posterior image 58. In more detail, referring now to FIG. 5, the whole body processing main panel 60 is shown. A new patient region 62 allows a user to select the patient from which the images are to be selected. When it is selected, the patient utilities menu 64 shown in FIG. 6 is displayed. The user is then prompted to select a patient. If the user selects a patient, the anterior, posterior, and geometric mean views and any associated regions of interest in the graphics screen layout 39, shown in FIG. 2 are cleared. This step is required to view images from a patient other than the current patient.

The anterior view region 66 allows a user to select the anterior view to be used. When it is selected, the patient utilities menu 64 shown in FIG. 6 is displayed and the user is prompted to select an image set. An image set is a set of images of portions of a whole body which when combined form a complete whole body image. The user is not allowed to change patients unless this is the first view being selected (i.e., a current patient has not been established).

A posterior view region 68 in the main panel 60 allows a user to select the posterior view to be used. When it is selected, the patient utilities menu 64 is displayed, and the user is prompted to select an image set. The user is not allowed to change patients unless this is the first view being selected. The geometric mean region 70 allows a user to select a previously created geometric mean image, or to create a new image. When the geometric mean region 70 is selected the user is prompted to determine if a new image is to be created in a selecting geometric mean panel 72 shown in FIG. 7. If the user wishes to load a previously created image, the patient utilities menu 64 is displayed and the user is allowed to select an image set. The user is not allowed to change patients unless this is the first view being selected (i.e., a current patient has not been established).

The geometric mean selection is shown in FIG. 4 as the alternative steps "create geometric mean image" 74 or "select previously created geometric mean" 76. The step of creating a geometric mean image 74, if selected, will cause the user to be prompted to provide a process and image set name for the image as shown in the "image name" screen 78 in FIG. 8. If the user has not selected an anterior view, he is prompted to do so at this time. The user is then instructed to select which quarter of the interior view to display as an expanded region. As shown in the "selecting expanded region" screen shown in FIG. 9. This portion selected must contain a feature which is discernable in both the interior and posterior views (ideally a point source.) A point source is more desirable than a feature within the body because it will not be attenuated by body tissue (being outside of the body), and so provides a sharply contrasted region in both views. Once the expanded region has been selected, the "boxing common feature" screen 82 shown in FIG. 10, appears which prompts the user to size and position a box so that it is centered over the feature. The box contains a cross-hair in its center to aid positioning. The box should be sized so that it just touches the edges of the feature. If the user has not selected a posterior view, he is prompted to select it at this time. The same lines from the posterior view as were displayed as the expanded anterior view are now displayed as the expanded region. The user is then prompted to move the previously sized box over the same feature as was boxed in the anterior image.

Once the user has defined the location of a common feature in the anterior 46 and posterior 48 views, the system 10 can then create a geometric mean image. This is accomplished by flipping the posterior view 48 around the y axis, aligning it over the anterior view 46, and taking the geometric mean between the overlaid pixels.

The reason for using the geometric mean is to compensate, or normalize, for sources at different depths in anterior 46 and posterior 48 images, to arrive at a calculated activity level which would be present if the source were at the midpoint of the body. This is desirable because it will be appreciated that activity (gama rays emitted by radiopharmaceuticals) that originates at differing levels within the body is attenuated by different amounts. This causes activity closer to the surface to appear hotter than activity further within the body. In this way, it can be viewed as a combination of the information present in both the anterior and posterior views. The theory behind the use of the geometric mean image for calculations is discussed below.

The counts detected in an anterior pixel due to a point source of activity can be represented as:

$$Ca = C * e^{-\mu * Da}$$

where:

$C$ = Counts at source
$\mu$ = Coefficient of attenuation
$Da$ = Depth of source from anterior view
and the posterior activity as:

$$Cp = C * e^{-\mu * Dp}$$

where:

$Dp$ = Depth of source from posterior view
and so the geometric mean value is:

$$\begin{aligned} Cm &= \sqrt{Ca * Cp} \\ &= (C * e^{-\mu * Da} * C * e^{-\mu * Dp})^{\frac{1}{2}} \\ &= C * e^{(-\mu * Da - \mu * Dp)/2} \\ &= C * e^{-\mu * (Da + Dp)/2} \end{aligned}$$

and since $(Da + Dp)$ is the total distance between views $$\begin{aligned} Cm &= C * e^{-\mu * Dmid} \\ &= \text{activity if point at mid-point of body} \end{aligned}$$

where:

$Dmid$ = Mid-point within body

Before the system 10 can create a geometric mean it must flip the posterior view around the Y axis, align it over the anterior view, and take the geometric mean between the overlaid pixels. Aligning the anterior and posterior views is accomplished by the following seven steps:

Step 1. Flip the posterior image around the y axis. This step is illustrated in FIG. 11 where blocks 84 and 86 illustrate representations of anterior and posterior images respectively. Block 88 illustrates the posterior view flipped about the y axis.

Step 2. Shift the boxed posterior feature by amounts from minus 4 to plus 4 pixels in the x direction and determine the cross-correlation at each shift, then shift the box by the amount which yields the maximum correlation. This step is depicted in box 90 in FIG. 11. The cross-correlation is calculated in two steps. First, all lines within a region are summed together to produce a single line of activity. The cross-correlation is then calculated as the square root of the sum of the squares of the difference in activity between corresponding points in the anterior and posterior lines of activity.

Step 3. Shift the x shifted boxed posterior feature by amounts from minus 4 to plus 4 pixels in the y direction and determine the cross-correlation at each shift. Shift the box by the amount which yields the maximum correlation. Step three is depicted in box 92 with the image shown in the correlated position.

Step 4. Perform step 2 again on the shifted posterior feature, this can result in greater accuracy in the alignment.

Step 5. Calculate the sum of the difference in the starting position of the anterior and posterior feature boxes in the x direction, and the amount needed to obtain the maximum correlation of the boxed feature. Next, shift the posterior image by this amount. The purpose of step 5 is to align the anterior and flipped posterior images in the X direction.

Step 6. Calculate the sum of the difference in the starting position of the anterior and posterior feature boxes in the y direction and the amount needed to obtain the maximum correlation of the boxed feature. Next, shift the posterior image by this amount. The purpose of step 6 is to align the anterior and flipped posterior images in the Y direction.

Step 7. Overlay the anterior and shifted posterior images. Each pixel of the geometric mean image is determined as the square root of the product of the corresponding anterior pixel and the shifted posterior pixel. If a posterior pixel does not overlap an anterior pixel, the geometric mean pixel is set to the anterior value. If the product of the anterior and posterior pixels is zero, the geometric mean pixel is set to the average of the two pixels.

Once the geometric mean image has been created (block 74 in FIG. 2), or a previously created geometric mean image is selected, block 76 in FIG. 4, The Whole Body Imaging System 10 proceeds to the "defined active area" block 94 shown in FIG. 4. The define active area selection, block 63 shown in FIG. 5, allows to user to define the area within a view which is to be used in calculating total and background corrected body counts. When it is selected, the user is asked to select which view to use in the "selecting image to view" screen 96, shown in FIG. 12. Next, the user is prompted to select the view's image set if one is not already selected. The user is then prompted to size and position a rectangle so that it just touches the edges of the patient's body in accordance with the "rectangle position" screen 98 shown in FIG. 13. The point source used to align the anterior and posterior views should ideally be outside the rectangle positioned in screen 98 so that it does not contribute to the body counts. When the user has positioned the rectangle and clicked button one, the area outside of this rectangle is shaded in red and is excluded from body count calculations.

Next, the user proceeds to the region statistics selection, block 65 in FIG. 5, which allows the user to create organ and background regions of interest (ROI's over a view). These steps are shown as boxes 100, 102, 104 and 106 in FIG. 4. Initially, the user is asked whether he wishes to create a new ROI, or load a previously created one in screen 108 shown in FIG. 14. If he selects to load an old ROI, he is prompted for the ROI type and the active view it is to be displayed over in screen 110. The patient utility menu 64, in FIG. 6, is displayed to allow him to select the ROI.

If the user chooses to create an ROI, panel 112 in FIG. 16, is displayed to allow the user to select the process and region names, as well as the type of ROI, which view it will displayed over, and the creation method to use. The default process name is Whole Body Processing. The default region name is a combination of the view it is to be displayed over and the type of ROI (i.e. anterior organ), and is changed automatically as the user changes these settings. Once the user has filled in the selections, a new process is created if needed and a new region set is created. If the desired view has not been selected, the patent utilities menu 64 is displayed and the user is asked to selected the view's image set. The view is then displayed, and the user is asked to select the portion of the view which contains the region of interest. This is done using panel 80 in FIG. 9. Once this is complete, the user is asked to create the region of interest using the selected creation method in the expanded region area. When the ROI is created, the statistics area is updated.

The expand view selection, block 67 in FIG. 5, allows the user to expand a portion of any view, and display it in greater detail in panel 50 in FIG. 2. When it is selected, the patient utilities menu 64 is displayed and the user is prompted to select the view. The view is then displayed if it is not already, and a square of one quarter of the view's area is displayed over the image. The user then holds down button one and slides the square over the image until it encloses the region to expand. When button one is released, the desired area is displayed in panel 50 in FIG. 2.

The next step is the note regions statistics" block 118 in FIG. 4. As discussed previously, the image statistics are displayed in panel 52 of screen layout 39 shown in FIG. 2. These statistics include the anterior, posterior, and geometric mean statistics for total body counts and raw organ as well as percentage whole body counts for the organ.

Finally, the "save expanded portions of images" step 120, in FIG. 4 is performed. The "save expanded view" selection, block 69 in FIG. 5, allows a user to save the portion of the view displayed in the expanded view area, along with any displayed ROI's. This is useful as a means of converting a part of a whole body image into a square image, which can be used by other processing applications. When save expanded view is selected, the user is first asked whether to also save ROI's which are displayed over the expanded region (if any ROI's are displayed) in the panel 114 in FIG. 17. The user is then prompted to supply a process, image set, and region set name in panel 116, in FIG. 18. If no ROI's are displayed, or the user chose not to save the displayed ROI, the region set name is set to "----" and cannot be changed. If any images have been previously saved for the current patient during the session, the process where the images were saved is the default process. If a new process is needed, it is created, and an image set containing a single image is created. The default name of the image set is a combination of the view and the lines of the view which make up the image (i.e. anterior lines 115-242). The dimensions of the image are the same as the x dimension of the view. If the user asked to save displayed ROI's, an ROI set is created and any displayed ROI's or portions of ROI's are saved. The default ROI set name is the same of the image set name. The region names are "Background ROI" and "Organ ROI".

From the foregoing it can be seen that the present invention provides a system and method for the quantitation of whole body distribution of radiopharmaceuticals which produces fast and accurate results even for organs that are not well visualized in only one view. Those skilled in the art can appreciate that other advantages can be obtained from the use of this invention, and that modification can be made without departing from the true spirit of the invention after studying the specification, drawings and following claims.

We claim:

1. A method for determining percentage uptake of a radiopharmaceutical in a selected region of a person's body, said method comprising the steps of:
   a. administering said radiopharmaceutical to said person;
   b. measuring a number of anterior counts on a scintillation detector emitted by said body at individual anterior coordinate locations from an anterior view to create an anterior image of said body;
   c. measuring a number of posterior counts on the scintillation detector emitted by said body at individual posterior coordinate locations from a posterior view to create a posterior image of said body;
   d. for each anterior coordinate location, determining the corresponding posterior coordinate location;
   e. calculating the geometric mean of anterior and posterior counts for each coordinate location to generate a geometric mean image of said body, wherein each coordinate location in said geometric mean image represents the geometric mean of the anterior and posterior counts for the coordinate location;
   f. calculating a total number of counts in said geometric mean image of both a selected region and of said body; and
   g. dividing said total number of counts in said geometric mean image of said selected region by the total number of counts in said geometric mean image of said body to determine the percentage uptake of said radiopharmaceutical in said selected region.

2. The method of claim 1 wherein said step b includes the step of displaying said anterior image on a CRT, and step c includes the step of displaying said posterior image on a CRT.

3. The method of claim 1 wherein the step of calculating the geometric mean further comprises the step of: calculating the geometric mean of the counts in the coordinate locations ($C_m$) as: $C_m = \sqrt{C_a \times C_p}$, where $C_a$ equals the counts detected in one of said anterior coordinate locations, and $C_p$ equals the counts detected in one of said posterior coordinate locations, and $C_m$ is the geometric mean of the counts in each coordinate location.

4. The method of claim 1 wherein said posterior and anterior images contain an x and y axis and said step d further includes the steps of:
   flipping the posterior image around the y axis;
   shifting the posterior image by discrete amounts in the x direction and determining a correlation for each shift;
   selecting the shifted position which yields the maximum of said correlations for each x direction shift;
   positioning the posterior image to said selected shifted position yielding said maximum;
   shifting said positioned posterior image in the y direction, and determining a correlation for each shift;
   selecting a final shifted position which yields the maximum of said correlation for each y direction shift; and
   overlaying the anterior and said final shifted position posterior images.

5. A system for determining percentage uptake of a radiopharmaceutical in a selected region of a person's body, said system comprising:
   a scintillation detector means for measuring a number of anterior and posterior counts emitted by said body at individual anterior and posterior coordinate locations from anterior and posterior views to create anterior and posterior images of said body;
   means for determining the posterior coordinate location which corresponds to each anterior coordinate location;
   means for calculating a geometric means of the anterior and posterior counts for each coordinate location to generate a geometric mean image of said body, wherein each coordinate location in said geometric mean image represents the geometric mean of the anterior and posterior counts for the coordinate location; and
   means for dividing a total number of counts in said geometric mean image of a selected region by a total number of counts in said geometric mean image of said body to determine the percentage uptake of said radiopharmaceutical in said selected region.

6. The system of claim 5 wherein the means for calculating the geometric mean further comprises a means for calculating the geometric mean of counts in the coordinate locations ($c_m$) as: $c_m = \sqrt{c_a \times c_p}$, where $c_a$ equals the counts detected in one of said anterior coordinate locations, $c_p$ equals the counts detected in one of said posterior coordinate locations, and $c_m$ is the geometric mean of the counts in each coordinate location.

7. The system of claim 5 wherein said posterior and anterior images contain an x and y axis and wherein the means for determining the corresponding posterior coordinate location for each anterior location further comprises:
   means for flipping the posterior image around the y axis;
   means for shifting the posterior image by discrete amounts in the x direction and determining a correlation for each shift;
   means for selecting the shifted position which yields the maximum of said correlations for each x direction shift;
   means for positioning the posterior image to said selected shifted position yielding said maximum;

means for shifting said positioned posterior image in the y direction, and determining a correlation for each shift;

means for selecting a final shifted position which yields the maximum of said correlations for each y direction shift; and means for overlaying the anterior and said final shifted position posterior images.

8. A method for the quantitation of whole body distribution of radiopharmaceutical in a body said method comprising the steps of:

administering said radiopharmaceutical to said person;

measuring a number of anterior counts on a scintillation detector emitted by said body at individual anterior coordinate locations from an anterior view to create an anterior image of said body;

measuring a number of posterior counts on the scintillation detector emitted by said body at individual posterior coordinate locations from a posterior view to create a posterior image of said body;

for each anterior coordinate location determining the corresponding posterior coordinate location;

calculating the geometric mean of the anterior and posterior counts for each coordinate location; and generating a geometric mean image of said body.

9. The method of claim 8 wherein said step of measuring the number of anterior counts, includes the step of displaying said anterior image on a CRT.

10. The method of claim 8 wherein the step of calculating the geometric mean further comprises the step of:

calculating the geometric mean of the counts in the coordinate locations ($C_m$) as: $C_m = \sqrt{C_a \times C_p}$, where $C_a$ equals the counts detected in one of said anterior coordinate locations, $C_p$ equals the counts detected in one of said posterior coordinate locations, and $C_m$ is the geometric mean of the counts in each coordinate location.

11. The method of claim 8 wherein the step of determining the corresponding posterior coordinate location further comprises the steps of:

flipping the posterior image around the y axis;

shifting the posterior image by discrete amounts in the x direction and determine a correlation for each shift;

selecting the shifted position which yields the maximum of said correlations for each x direction shift;

positioning the posterior image to said selected shifted position yielding said maximum;

shifting said positional posterior image in the y direction, and determining a correlation for each shift;

selecting a final shifted position which yields the maximum of said correlation for each y direction shift; and overlaying the anterior and said final shifted position posterior images.

* * * * *